United States Patent [19]
Jiraki

[11] Patent Number: 5,701,918
[45] Date of Patent: Dec. 30, 1997

[54] MEDICAL GLOVE FOR FACILTIATING ENDOTRACHEAL INTUBATION AND METHOD OF USING SAME

[76] Inventor: Kalil M. Jiraki, 6751 Grandmont, Detroit, Mich. 48228

[21] Appl. No.: 673,353

[22] Filed: Jun. 23, 1996

[51] Int. Cl.⁶ ............................................. A61B 17/00
[52] U.S. Cl. ............................................. 128/897; 606/1
[58] Field of Search ............................. 128/897, 898, 128/200.26, 207.14; 2/19, 159, 160, 161.6, 161.7, 162–164; 606/1; 604/28

[56] References Cited

U.S. PATENT DOCUMENTS

| | | | |
|---|---|---|---|
| 4,665,561 | 5/1987 | Aoki | 2/19 |
| 4,766,612 | 8/1988 | Patton | 2/163 |
| 4,919,966 | 4/1990 | Shlenker | 2/168 |
| 5,263,478 | 11/1993 | Davis | 128/207.14 |

OTHER PUBLICATIONS

"A New tracheal tube for Difficult Intubation" West et al., British J. of Anaesthesia, 76, 673–679, 1996.

"A Multilunen Catheter Guide for Difficult Airway Management", Dhara, Anaesthesia, 49, 974–978, Jan. 1994.

"A New Tracheal Tube for Difficult Intubation" M. West, M. Jonas, A. Adams and F. Carli, British J. of Anaesthesia, 76, 673–679, 1996.

"A Multilumen Catheter Guide for Difficult Airway Management" S. Dhara, Anaesthesia, 49, 974–978, 1994.

*Primary Examiner*—Jennifer Bahr
*Assistant Examiner*—David Ruddy
*Attorney, Agent, or Firm*—Peter D. Keefe; William D. Blackman

[57] ABSTRACT

A medical glove for use in endotracheal intubations having one or more finger extension members attached to and extending outwardly from fingertip portions of one or more finger covers thereof. The finger extension members are useful in manipulating soft throat and mouth parts to assist in placement of an endotracheal tube into a patient's trachea, to thereby provide a functional airway where normal breathing is stopped or impaired. A method of performing an endotracheal intubation involves using the finger extension members of the medical glove to reach into a patient's throat to move the patient's tongue forwardly in the patient's mouth and to secure the larynx, followed by inserting an endotracheal tube into the patient's trachea.

20 Claims, 2 Drawing Sheets

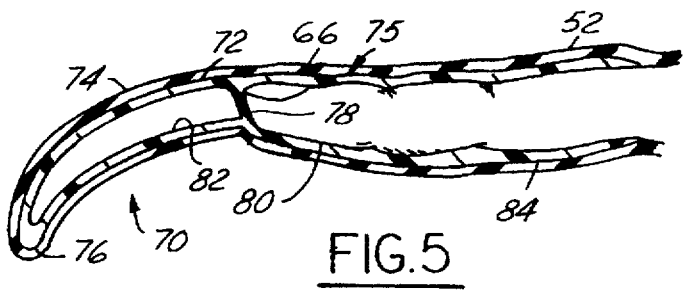
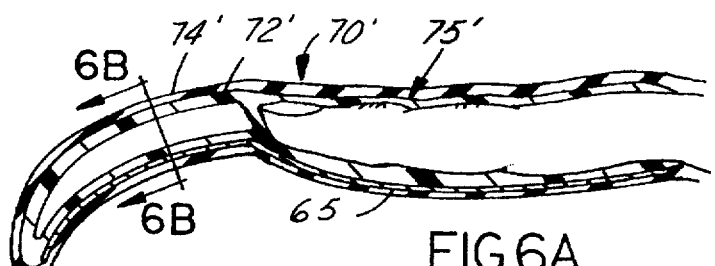
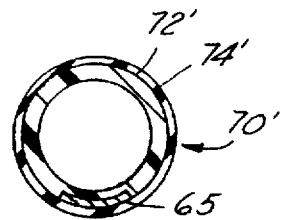
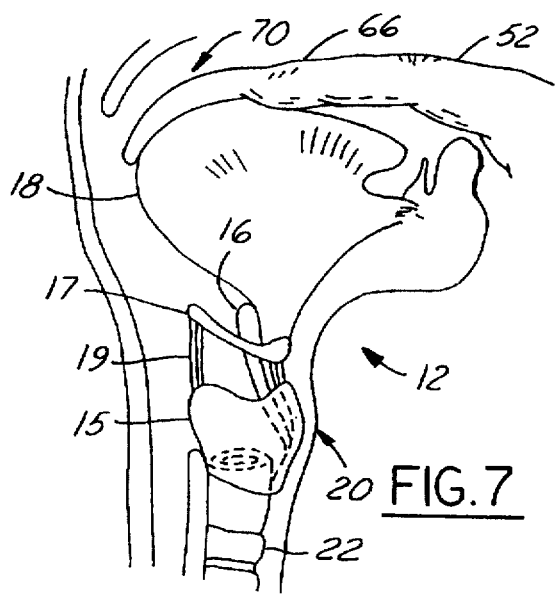
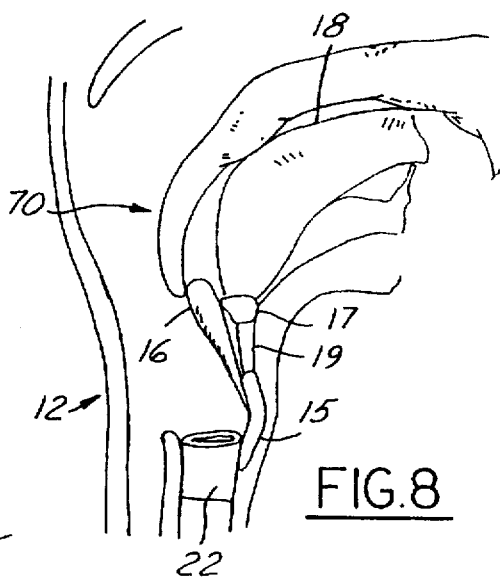
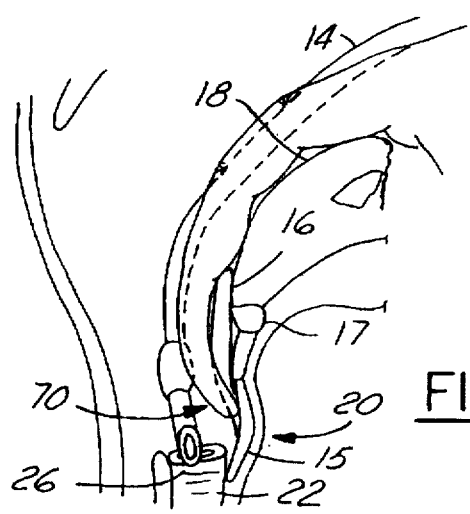

MEDICAL GLOVE FOR FACILITATING ENDOTRACHEAL INTUBATION AND METHOD OF USING SAME

BACKGROUND OF THE INVENTION

1. Field of the Invention

The present invention relates to medical tools and procedures. More particularly, the present invention relates to a medical glove for use by a doctor or other medical caregiver in performing an endotracheal intubation.

2. Description of the Prior Art

Endotracheal intubation is a life saving medical procedure in which a medical caregiver places a tube down a patient's respiratory tract to provide or ensure a functional air passage when normal air flow is obstructed in some way, or when the patient is unable to breathe on his or her own.

As discussed on page 553 of *Comprehensive Respiratory Care*, D. H. Eubanks et al., The C. V. Mosby Co., 1990, endotracheal intubation is most commonly used in conditions of, or leading to, respiratory failure, such as:

trauma to the airway or chest;

neurologic involvement from drugs, myasthenia gravis, poisons, etc.;

cardiovascular involvement leading to central nervous system impairment from strokes, tumors, trauma, infection, or pulmonary emboli;

pulmonary impairment from aspirants, infections, tumors, trauma, pneumonia, poisons, pneumothorax, chronic obstructive pulmonary disease, surgery, or bronchiectasis; or cardiopulmonary arrest.

For example, sometimes an allergic reaction of the throat, due to bee stings or other stimuli, can cause the throat to swell to such an extent that it blocks air flow through the larynx, thus posing a serious health risk to the patient, As a result, it becomes necessary to place a tube into the patient's breathing passage to provide a functional airway for the patient, Alternatively, during surgery, an anaesthesiologist may need to administer a muscle relaxant which temporarily inhibits the patient's breathing process, necessitating the use of an external respirator until the drug wears off. In such a case, an endotracheal tube must be inserted into the patient's trachea for connection to the external respirator.

Referring now to FIGS. 1 through 3, the head 10 of a patient 12 is shown in a tilted back position because, traditionally, in order to perform an endotracheal intubation, a medical caregiver would have to tilt a patient's head back to see into the patient's throat to ensure proper placement of an endotracheal tube 14. For purposes of hereinbelow elaborating the present invention and this present discussion, the larynx 20 includes the following components. The thyroid cartilage 15, which is generally cup-shaped, is connected to the hyoid bone 17 by the thyrohyoid membrane 19. The patient's epiglottis 16 is a movable flap of tissue which is located behind the base of the tongue 18 and is connected to the thyroid cartilage 15. The epiglottis 16 acts as a valve to help guide the flow of food and air entering the throat into the esophagus 24 and trachea 22, respectively. The trachea 22, which is commonly called the windpipe, is located below and connected to the larynx 20, and is disposed toward the front of the throat, The esophagus 24 is a food passageway that is located in the throat behind the trachea 22 and runs substantially parallel thereto. During normal breathing, as shown in FIG. 2, the epiglottis 16 is folded upwardly out of the way and allows air to pass through the larynx 20, which is the entrance to the respiratory tract, After passing through the larynx 20, air passes into the trachea 22. During swallowing, the epiglottis 16 is folded backwardly to cover and obstruct the larynx 20, directing food therepast and back to the esophagus 24.

During endotracheal intubation, a medical caregiver guides an endotracheal tube 14 between a patient's vocal cords 26 and into the larynx 20 of a patient 12, from which it passes into the trachea 22, to provide or ensure a functional air passage for the patient, However, during the procedure of inserting the endotracheal tube 14 down the throat of a patient 12, if a medical caregiver is inexperienced or is not exceptionally careful, it is easy to place the endotracheal tube down the esophagus 24 instead of the trachea 22, which can lead to delays and to serious medical complications. It is particularly important, during the endotracheal intubation procedure, to move the tongue 18 forwardly and to hold the larynx 20 securely, in order to gain access to the trachea 22, so that the endotracheal tube 14 may be correctly inserted therein.

Sometimes, at an accident scene, a patient has stopped breathing and has also suffered neck trauma. An EMS technician on the scene might have no choice but to tilt the patient's head 10 back, to a position similar to that shown in FIG. 2, in order to look into the throat and see where to place the endotracheal tube 14, despite the risk of exacerbating any existing spinal damage, since immediate resumption of the patient's breathing is essential. Therefore, it would be advantageous if a procedure were available to perform an endotracheal intubation without tilting the patient's head back.

As shown in FIG. 1, an endotracheal tube 14 generally has a curved tube body 28 with a beveled end 30 for placement within a patient's trachea 22. The tube body 28 has an inflatable cuff 32 mounted thereon proximate the beveled end 30 thereof. A cuff tube 34 is provided to fill the cuff 32, to thereby form a seal between the endotracheal tube 14 and the trachea 22 after it has been placed thereinside. A proximal end 36 of the endotracheal tube 14 is located opposite the beveled end 30, and the proximal end conventionally has a 15 millimeter adapter 38 thereon for connecting to a machine respirator (not shown).

Endotracheal tubes are usually constructed of natural rubber, polyvinyl chloride, silicone rubber, nylon, or tetrafluoroethylene, commonly referred to by the trademark "TEFLON", or by a combination of the above materials. Sometimes a metal stylet (not shown) is placed inside the endotracheal tube during insertion thereof, to provide strength and to help guide the tube into place.

The tools available to a medical caregiver for performing an endotracheal intubation include laryngoscopes, assorted hand-held metal or plastic manipulators and normal surgical gloves. However, many of the available hand-held manipulators are formed of hard and inflexible materials, and may cause soft tissue damage when used to move the tongue and epiglottis out of the way of the larynx. Laryngoscopes may also damage soft tissues and further pose a risk of displacing teeth if not carefully and properly used. Another disadvantage of these presently available tools is that laryngoscopes and manipulators provide little or no tactile interaction to the medical caregiver, and while surgical gloves do provide tactile interaction, they do not normally provide sufficient depth of reach to enable a medical caregiver to reach the larynx.

Therefore, there is a need in the medical art for a tool which is resiliently deformable, yet which has some significant degree of strength and structural integrity, to manipulate soft tissue in endotracheal intubation procedures, without substantially damaging the soft tissues being held or supported. Preferably, such a tool would provide tactile interaction to a user thereof and would be usable according to a procedure which did not require tilting a patient's head back.

SUMMARY OF THE INVENTION

The present invention provides a medical glove for performing endotracheal intubations, and also provides a method of using the medical glove in performing an endotracheal intubation, which enables a medical caregiver to place an endotracheal tube into a patient's trachea in a matter of seconds and without tilting the patient's head back.

The present invention provides a medical glove which has one or more finger extension members attached to and extending beyond respective finger covers thereof. The finger extension members of the medical glove are usable to manipulate soft tissues in medical procedures, and are particularly useful in performing endotracheal intubations. The finger extension members of the medical glove according to the present invention are somewhat soft and resiliently deformable to minimize soft tissue damage during use.

The medical glove in accordance with the present invention includes a glove body for covering a hand of a user, the dove body including a center section for surrounding and enclosing a central portion of a user's hand. The center section of the medical glove has a base with an opening formed therein for receiving a user's hand. A series of four finger covers are attached to the center section for receiving the fingers of a user's hand therein, and each finger cover has a fingertip portion for covering a fingertip. A thumb cover is also attached to the center section for receiving a thumb of a user's hand therein. At least one finger extension member is provided attached to a fingertip portion of one of the finger covers and extends therebeyond, the finger extension member including a substantially tubular projection for manipulation by a wearer of the medical glove. In a preferred embodiment, the medical glove has a first finger extension member attached to a center finger cover, and a second finger extension member attached to an index finger cover. The finger extension member or members may be made solid or may each have a sealed cavity formed therein, which may be filled with a fluid or a foam. An elongated insert may be provided for the projection, to help provide stiffness and add definition thereto.

The present invention also encompasses a method of performing an endotracheal intubation using the medical glove according to the invention. The first step in the method is placing a medical glove on a medical caregiver's hand, the medical glove being configured as described hereinabove. The next step in the method according to the present invention is using the fingertip extension members of the medical glove to hold a patient's larynx and tongue securely in the patient's mouth. The last step in the method according to the present invention is slidingly inserting an endotracheal tube into the patient's trachea, while the finger extension members are securing the larynx, to provide an air conduit for the patient. Where the aforementioned preferred medical glove having dual finger extension members is used, the endotracheal tube may be inserted between the two finger covers which bear the finger extension members to perform the inserting step.

Accordingly, it is an object of the present invention to provide a medical glove, and a procedure of using the medical glove, which will minimize soft tissue damage during an endotracheal intubation procedure.

It is a further object of the present invention to provide a medical glove having four finger covers, at least one of the finger covers having a finger extension member attached thereto for use as a medical tool in manipulating soft tissues during an endotracheal intubation procedure.

It is yet a further object of the present invention to provide a medical glove, and a procedure of using the medical glove, which will minimize the time required to perform an endotracheal intubation when time is a critical factor.

It is yet another object of the present invention to provide a method of inserting a tracheal tube into a patient's trachea, which can be done without requiring a medical caregiver to tilt the patient's head back during the procedure.

These, and additional objects, advantages, features and benefits of the present invention will become apparent from the following specification, which should be read in conjunction with the accompanying drawings.

BRIEF DESCRIPTION OF THE DRAWINGS

FIG. 5 is a cross-sectional view of a finger cover and finger extension member of the medical glove according to the present invention, taken along the line 5—5 of FIG. 4, wherein a user's fingertip is shown there.

FIG. 6A is a cross-sectional view of a finger cover and finger extension member of the medical glove according to the present invention similar to FIG. 5, now showing an alternative embodiment of the present invention.

FIG. 6B is a cross-sectional view of a finger extension member according to the alternative embodiment of the present invention, seen along line 6B—6B in FIG. 6A.

FIG. 7 is a partly cut-away view of a patient's mouth and neck, with the head in an upright position, wherein a pair of finger extension members of the medical glove according to the preferred embodiment of the present invention are being placed into the patient's mouth.

FIG. 8 is a partly cut-away view of the patient's mouth and neck as generally shown in FIG. 7, wherein the pair of finger extension members of the medical glove according to the preferred embodiment of the present invention have been slid over the patient's tongue and epiglottis.

FIG. 9 is partly cut-away view of the patient's mouth and neck as generally shown in FIG. 7, wherein the finger extension members of the medical glove according to the present invention have now secured the patient's larynx while keeping the patient's tongue pulled forwardly, and wherein an endotracheal tube has been slidably inserted into the patient's trachea.

DETAILED DESCRIPTION OF THE PREFERRED EMBODIMENT

Figure 4:
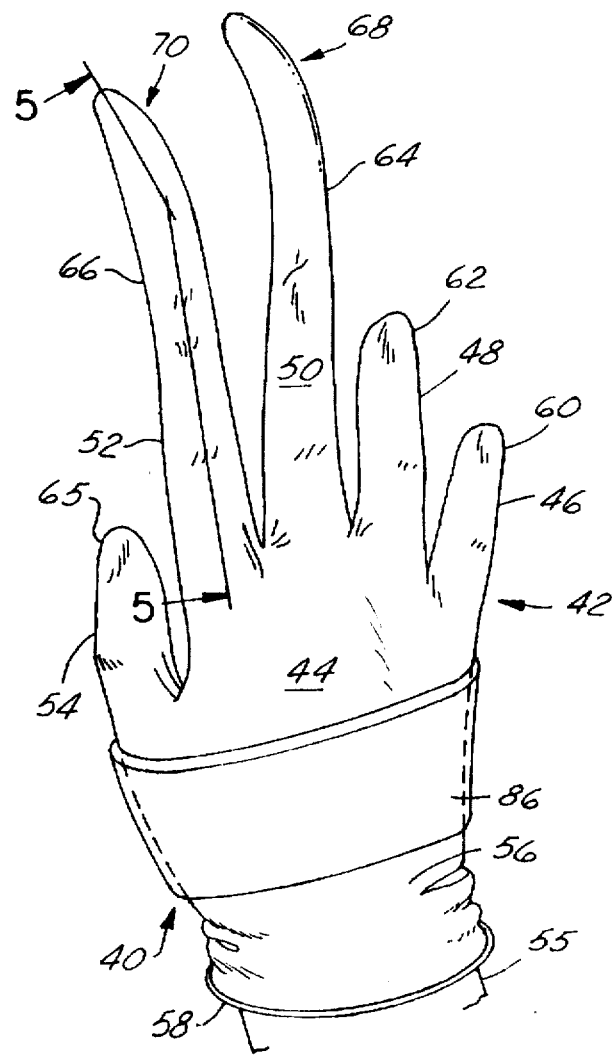
FIG. 4 is a perspective view of a medical glove according to a preferred embodiment of the present invention, mounted on a user's hand.

Referring now to the Drawings, FIG. 4 shows a medical glove 40 according to the present invention for facilitating the placement of an endotracheal tube into the trachea of a non-breathing patient, to thereby provide a functional air passage to get the patient breathing again. The medical glove 40 according to the present invention is intended to be used without a conventional laryngoscope.

Figure 1:
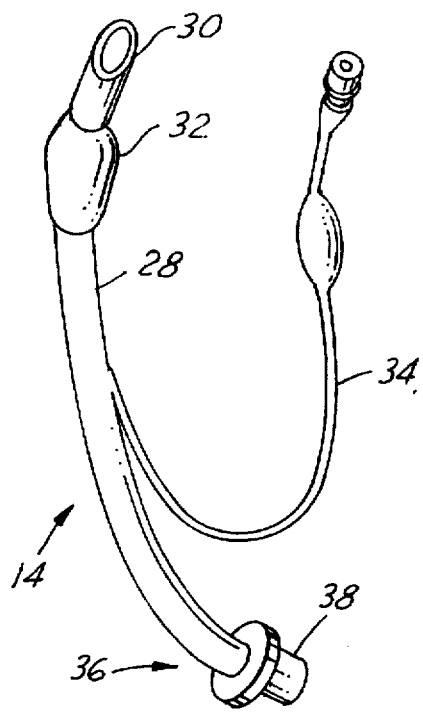
FIG. 1 is a perspective view of a prior art endotracheal tube.
Figure 2:
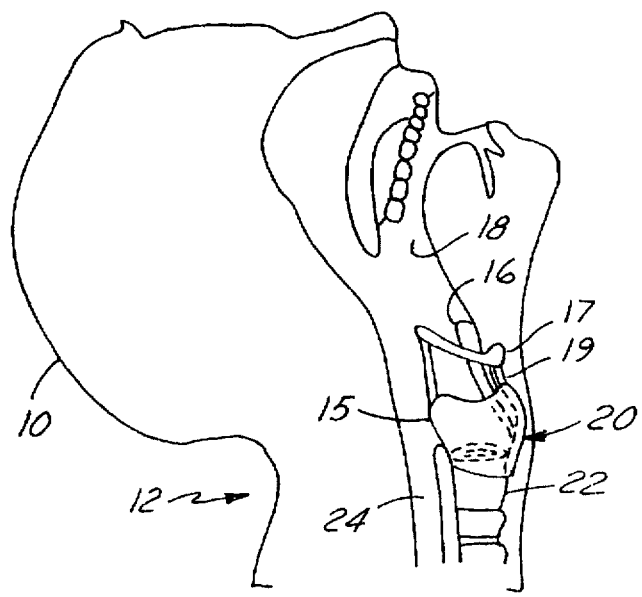
FIG. 2 is a partly cut-away view of a patient's head and neck in a tilted back position, showing the respiratory tract thereof.

With proper training and experience, the medical glove 40 may be used to perform guided blind intubations, that is, to aid a medical caregiver in inserting an endotracheal tube 14 into a patient's trachea 22 without looking into the throat (see FIGS. 1 and 2). Such a guided blind intubation procedure allows the medical caregiver to place the endotracheal tube into the patient's trachea without requiring the medical caregiver to tilt the patient's head back, as has been customary in prior practice. A guided blind intubation without tilting a patient's head back may be very advantageous in a case where a patient has suffered neck trauma. Also, doing a guided blind intubation takes only a few seconds, whale a conventional intubation, in which the patient's head is tilted back and the medical caregiver looks into the throat, is considerably more time-consuming than a guided blind intubation, in a situation where time is critical. Accordingly, because of its shorter duration, a guided blind intubation minimizes any risk of brain injury from lack of oxygen due to arrested breathing.

Figure 3:
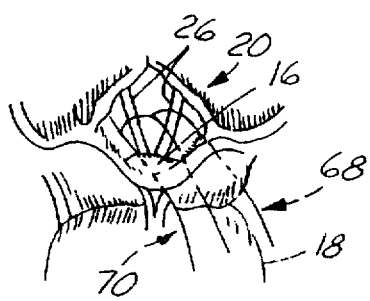
FIG. 3 is a detail environmental view of a patient's throat from the point of view of a medical caregiver looking into the mouth, with finger extension members of a medical glove according to the present invention being shown in phantom.

While FIG. 3 shows the tongue 18, the larynx 20, and the vocal cords 26 as seen from a point of view of a medical caregiver looking into the patient's throat, this view is intended for purposes of illustration only, and is not meant to suggest that the medical caregiver needs to look down the patient's throat to perform the procedure hereof. As previously noted, the method of the present invention is intended to be performed, after proper training and practice on a manikin, without requiring the medical caregiver to look into the patient's throat.

As shown in FIG. 4, the medical glove 40 according to the present invention includes a hollow glove body 42 for covering a hand 55 of a user. The glove body 42 is preferably formed of latex rubber via a latex dipping process. The glove body 42 includes a center section 44 for surrounding and enclosing a central portion of a user's hand. Four finger covers 46, 48, 50, 52, and a thumb cover 54 are attached to the center section 44, as will be further defined herein. The center section 44 also has a base 56 with an opening 58 formed therein for receiving a user's hand 55 so that the medical glove 40 can be put on.

The glove body 42 includes a little finger cover 46 attached to the center section 44 for receiving a little finger of a user's hand there, wherein the little finger cover has a fingertip portion 60 for covering the user's little fingertip.

The glove body 42 also includes a ring finger cover 48 attached to the center section 44 for receiving a ring finger of a user's hand therein, wherein the ring finger cover has a fingertip portion 62 for covering the user's ring fingertip.

The glove body 42 further includes a center finger cover 50 attached to the center section 44 for receiving a center finger of a user's hand therein, wherein the center finger cover has a fingertip portion 64 for covering the user's center fingertip.

The glove body 42 further includes an index finger cover 52 attached to the center section 44 for receiving an index finger of a user's hand therein, wherein the index finger cover has a fingertip portion 66 for covering the user's index fingertip.

The glove body 42 further includes a thumb cover 54 attached to the center section 44 for receiving a thumb of a user's hand therein, wherein the thumb cover includes a thumbtip portion 65 for covering the user's thumbtip.

In the preferred embodiment hereof, as shown in FIG. 4, both the center finger cover 50 and the index finger cover 52 have finger extension members 68 and 70 attached to their respective fingertip portions 64 and 66 and extending axially therebeyond.

The following discussion of the structure of the finger extension member 70 of the index finger cover 52 applies equally to a finger extension member for any other finger cover or for the thumb cover, since these finger extension members have a substantially identical structure to that of the finger extension member 70 for the index finger cover.

The finger extension member 70 is provided in the medical glove 40 for extending the reach of a user's finger while providing tactile sensation to a medical caregiver who is wearing the medical glove. The finger extension member 70 ends in a rounded tip 76. The index finger cover 52, shown as an illustrative example, is formed around and is attached to an inner support member 75 (see FIG. 5).

As seen in FIG. 5, the finger extension member 70 includes an inner support member 75, which is surrounded and anchored in place by an outer layer 74 of conventional latex rubber or other flexible and tear-resistant material, which is the same material making up the glove body 42. The inner support member 75 is preferred to be made out of a somewhat flexible, yet strong polyurethane or other suitable elastomer for a combination of strength and limited flexibility. The inner support member 75 includes a concavely shaped cross-wall 78 for contacting the tip of a user's finger 80, the cross-wall being disposed substantially perpendicular to a longitudinal axis of the finger cover 52. The inner support member 75 also includes a substantially tubular projection 72, which curves downwardly as it extends forwardly from the cross-wall 78. The projection 72 may be solid, or alternatively, the interior of the projection may be hollow, wherein a sealed cavity 82 extends therein between the cross-wall and the rounded tip 76. Where present, the cavity 82 may be filled with air, another fluid, or foam to help provide stiffness and add tactile definition to the finger extension member 70.

The inner support member 75, preferably, also includes an integrally formed, substantially cylindrical sleeve 84 extending rearwardly from the cross-wall 78, opposite the projection 72, which is structured to receive and support a finger 80 therein. The sleeve 84 provides strength and support to the finger extension member 70 of the medical glove 40 to aid a medical caregiver in using the finger extensions 68, 70 to manipulate a patient's tongue and larynx in performing an endotracheal intubation procedure. In the preferred embodiment of the present invention, the sleeve 84 extends through the entire length of the finger cover 52 to cover the entire finger 80 of a user. The finger cover 52 which bears the finger extension member 70 may appear substantially thickened, as shown in FIG. 5, where the finger cover 52 overlaps the sleeve 84.

In an alternative embodiment shown in FIGS. 6A and 6B, the inner support member 75' may include a reinforcement member 65 which is inset at a centrally disposed portion thereof, extending therealong and covered by the outer layer 74'. The reinforcement member 65 is preferably a metallic or plastic material which provides stiffness and adds tactile definition to the projection 72' of the finger extension member 70'.

As shown in FIG. 4, the center section 44 of the medical glove 40 preferably includes a bite guard 86 in the form of a thickened band attached to and encircling the palm and the back of the hand of a user, for protecting the user of the medical glove from being inadvertently bitten by a patient during an intubation procedure. The bite guard 86 is formed of a tough, tear-resistant rubber or elastomeric material attached to the center section 44 of the glove body 42.

The present invention also encompasses a method of performing an endotracheal intubation using the medical glove 40. In this regard, FIGS. 7 through 9 illustrate a sequence of steps in the method hereof on a patient 12 with the patient's head in a fully upright position. In FIG. 7, a medical caregiver's hand, wearing the medical glove 40 according to the present invention, inserts the finger extension members 68, 70 into the mouth of the patient 12. In FIG. 8, the medical caregiver has located the finger extension members 68, 70 over and behind the patient's tongue 18 and is preparing to hold the larynx 20 in place. In FIG. 9, the tongue 18 has now been pulled as far forwardly as is practicable, the larynx 20 is secured by the finger extension members 68, 70 and an endotracheal tube 14 is being inserted between the index and center finger covers 50, 52, past the patient's vocal cords 26, and into the patient's trachea 22. Where dual finger extension members 68, 70 are used, the endotracheal tube 14 is preferably said between the finger covers 50, 52 which carry the finger extension members 68, 70 to thereby guide the endotracheal tube into place in the trachea 22.

As noted above, using the medical glove 40 according to the present invention, and with proper training and practice on artificial manikins, it is entirely feasible to perform a guided blind intubation, that is, an intubation guided by the finger extension members 68, 70 without viewing the inside of the throat, and further without tilting a patient's head backward (although this may still be done if desired and without injury to the patient). This allows for endotracheal intubation in a case where the patient may have suffered neck or spinal cord injury in an accident, while minimizing any risk of compounding or exacerbating any existing neck trauma. Also, a guided blind intubation using the medical glove 40 and method of the present invention minimizes the time needed for intubation, and restores the patient to breathing more quickly than conventional methods. This minimizes the risk of brain damage due to oxygen deprivation.

The following is a discussion of a preferred method of making the medical glove 40 of the present invention. Those practicing in the relevant art will realize that other equivalent methods of making the medical glove 40 may be used. The following discussion is intended to be illustrative, and not limitative.

In a preferred method of manufacture, the medical glove 40 according to the present invention is made in two stages.

In the first stage of manufacture, the support members 75 are manufactured by pouring and curing a selected polyurethane into a speedily designed mold (not shown). The preferred polyurethanes are polyurethane elastomers including polymeric isocyanates (PMDI) of various functionalities from 2.2 to 8.0, various adducts of di- or polymeric isocyanates, prepolymers or quasi-prepolymers consisting of a combination of polyether-, polyester-, and polybutadiene-based polyols with di- or polymeric isocyanates. The functionality of the polyols may vary from 2 to 8, and may also consist of blends of polyols having different functionalities. Chain extenders such as 1,4-BD, 1,4-HD, 2-methyl-pentanediol, etc. may be used, and where they are used, their presence will contribute to greater strength of the final elastomers. The curing conditions (temperature, time) of the polyurethane support members 75 will depend upon the type of polyurethane resin system used. Catalysts such as metal catalysts, e.g. tin catalysts, such as dibuutyl tin dilaurate, and tertiary amine catalysts (e.g. DABCO and NIAX A-1) may be used, as well as combinations thereof. Pigments such as silica, silicates, calcium carbonate, titanium dioxide, carbon black, ferric oxide, etc. may be used in the preparation of the polyurethane support members 75.

In the second stage of manufacture, the support members 75 are mounted onto a mold made in the shape of a hand, and the mold, with the support members attached thereto, is dipped into a latex rubber dipping solution. Latex rubber then adheres to the mold and to the support members 75 to form the medical glove 40 with the finger extension members 68, 70 made an integral part thereof. The medical glove 40 may be made in both a left-handed and a right-handed version.

If a foam or a fluid (fluid or gas) other than air is to be present in the cavity, the foam or fluid may be introduced thereinto during the first stage of manufacture.

The foregoing description is intended to be illustrative, and not restrictive. To those skilled in the art to which this invention pertains, the above described preferred embodiments may be subject to change or modification. Such change or modification can be carried out without departing from the scope of the invention, which is intended to be limited only by the scope of the appended claims.

What is claimed is:

1. A medical glove for manipulating tissues in medical procedures, comprising:
   a glove body for covering a hand of a user, said glove body comprising a center section for surrounding and enclosing a central portion of the hand, said center section having a base end with an opening formed there for receiving the hand, said glove body further comprising:
      a thumb cover attached to said center section for receiving therein a thumb of the hand, said thumb cover having a thumbtip portion;
      an index finger cover attached to said center section for receiving therein an index finger of the hand, said index finger cover having a first fingertip portion;
      a center finger cover attached to said center section for receiving therein a center finger of the hand, said center finger cover having a second fingertip portion;
      a ring finger cover attached to said center section for receiving there a ring finger of the hand, said ring finger cover having a third fingertip portion; and
      a little finger cover attached to said center section for receiving there a little finger of the hand, said little finger cover having a fourth fingertip portion; and
   at least one finger extension member connected with at least one of said thumbtip portion, said first fingertip portion, said second fingertip portion, said third fingertip portion, and said fourth fingertip portion and extending axially therefrom, said at least one finger extension member comprising a substantially tubular projection for being manipulated by the hand, wherein said at least one finger extension member forms an extension of the respective thumb cover, little finger cover, ring finger cover, center finger cover, and index finger cover to which said at least one finger extension member is attached;
   wherein said at least one finger extension member is solid.

2. The medical glove of claim 1, wherein said glove body has a palm; wherein said at least one finger extension member is curved, the curve being toward said palm.

3. The medical glove of claim 1, wherein said at least one finger extension member comprises:
   a first finger extension member connected with said first fingertip portion; and
   a second finger extension member connected with said second fingertip portion.

4. A medical glove for manipulating tissues in medical procedures, comprising:
   a glove body for covering a hand of a user, said glove body comprising a center section for surrounding and enclosing a central portion of the hand, said center section having a base end with an opening formed therein for receiving the hand, said glove body further comprising:
      a thumb cover attached to said center section for receiving therein a thumb of the hand, said thumb cover having a thumbtip portion;
      an index finger cover attached to said center section for receiving therein an index finger of the hand, said index finger cover having a first fingertip portion;
      a center finger cover attached to said center section for receiving therein a center finger of the hand, said center finger cover having a second fingertip portion;
      a ring finger cover attached to said center section for receiving therein a ring finger of the hand, said ring finger cover having a third fingertip portion; and
      a little finger cover attached to said center section for receiving therein a little finger of the hand, said little finger cover having a fourth fingertip portion; and
   at least one finger extension member connected with at least one of said thumbtip portion, said first fingertip portion, said second fingertip portion, said third fingertip portion, and said fourth fingertip portion and extending axially therefrom, said at least one finger extension member comprising a substantially tubular projection for being manipulated by the hand, wherein said at least one finger extension member forms an extension of the respective thumb cover, little finger cover, ring finger cover, center finger cover, and index finger cover to which said at least one finger extension member is attached; and
   a bite guard connected with said center section of said glove body, said bite guard comprising a band extending around said center section.

5. A medical glove for manipulating tissues in medical procedures, comprising:
   a glove body for covering a hand of a user, said glove body comprising a center section for surrounding and enclosing a central portion of the hand, said center section having a base end with an opening formed therein for receiving the hand, said glove body further comprising:
      a thumb cover attached to said center section for receiving therein a thumb of the hand, said thumb cover having a thumbtip portion;
      an index finger cover attached to said center section for receiving therein an index finger of the hand, said index finger cover having a first fingertip portion;
      a center finger cover attached to said center section for receiving therein a center finger of the hand, said center finger cover having a second fingertip portion;
      a ring finger cover attached to said center section for receiving therein a ring finger of the hand, said ring finger cover having a third fingertip portion; and
      a little finger cover attached to said center section for receiving therein a little finger of the hand, said little finger cover having a fourth fingertip portion; and
   at least one finger extension member connected with at least one of said thumbtip portion, said first fingertip portion, said second fingertip portion, said third fingertip portion, and said fourth fingertip portion and extending axially therefrom, said at least one finger extension member comprising a substantially tubular projection for being manipulated by the hand, wherein said at least one finger extension member forms an extension of the respective thumb cover, little finger cover, ring finger cover, center finger cover, or index finger cover to which said at least one finger extension member is attached;
   wherein said at least one finger extension member is hollow; said at least one finger extension member comprising an inner support member, wherein said inner support member is sealingly connected with said at least one finger extension member to thereby form a sealed cavity.

6. The medical glove of claim 5, wherein said cavity is filled with a material selected from at least one of a fluid and a foam.

7. The medical glove of claim 6, wherein said cavity is filled with air.

8. The medical glove of claim 5, wherein said inner support member is covered by a material that is integrally formed with said glove body.

9. The medical glove of claim 7, wherein said inner support member further comprises a sleeve extending along and inside the at least one of said thumb cover, said index finger cover, said center finger cover, said ring finger cover and said little finger cover.

10. The medical glove of claim 9, wherein said inner support member further comprises a reinforcement member substantially axially coextensive therewith.

11. The medical glove of claim 6, wherein said glove body has a palm; wherein said at least one finger extension member is curved, the curve being toward said palm.

12. The medical glove of claim 11, where said at least one finger extension member comprises:
   a first finger extension member connected with said first fingertip portion; and
   a second finger extension member connected with said second fingertip portion.

13. The medical glove of claim 12, further comprising a bite guard connected with said center section of said glove body, said bite guard comprising a band extending around said center section.

14. The medical glove of claim 13, where said inner support member further comprises a sleeve extending along, respectively, said index finger cover and said center finger cover.

15. The medical glove of claim 14, where said inner support member further comprises a reinforcement member substantially axially coextensive therewith.

16. The medical glove of claim 15, where said inner support member is covered by a material that is integrally formed with said glove body.

17. A method of performing an endotracheal intubation, the endotracheal intubation involving movement of a tongue and epiglottis of a patient in relation to a trachea of the patient, said method comprising the steps of:
   placing a fingertip extension member upon at least one fingertip of a hand of a medical caregiver;
   inserting the hand into the mouth of a patient, wherein the fingertip extension member is in a leading position relative to the hand;

manipulating the finger tip extension member to move the tongue and epiglottis of the patient to a position favorable for insertion of an endotracheal tube into the trachea of the patient, wherein the tongue and the epiglottis do not interfere with the insertion; and sliding an endotracheal tube into the trachea of the patient while the tongue and epiglottis are held in the position.

18. The method of claim 17, where said step of placing comprises placing a glove upon the hand.

19. The method of claim 18, wherein said step of placing further comprises:

placing a first finger extension member at an index finger fingertip of the medical caregiver; and placing a second finger extension member at a center finger fingertip of the medical caregiver.

20. The method of claim 19, wherein said step of sliding comprises:

sliding the endotracheal tube between the first finger extension member and the second finger extension member opposite the tongue and epiglottis.

* * * * *